United States Patent [19]

Fleming et al.

[11] 4,095,024
[45] June 13, 1978

[54] PROCESS FOR THE MANUFACTURE OF 1-ARYL-3-CARBOXYPYRAZOLID-5-ONES

[75] Inventors: Ian George Cameron Fleming; Raymond Vincent Heavon Jones, both of Manchester, England

[73] Assignee: Imperial Chemical Industries Limited, London, England

[21] Appl. No.: 653,832

[22] Filed: Jan. 30, 1976

[30] Foreign Application Priority Data

Jan. 31, 1975 United Kingdom .................. 4291/75

[51] Int. Cl.$^2$ .......................................... C07D 231/08
[52] U.S. Cl. .................................................. 548/367
[58] Field of Search ..................... 260/310 A; 548/367

[56] References Cited

U.S. PATENT DOCUMENTS

| 2,704,762 | 3/1955 | Kendall et al. .................. 260/310 A |
| 3,153,654 | 10/1964 | Ficken et al. ..................... 260/310 A |
| 3,178,441 | 4/1965 | Ficken et al. ..................... 260/310 A |

OTHER PUBLICATIONS

Vystrcil et al., Chemical Abstracts, vol. 46, 7566, (1952).
Bouchet et al., Chem. Abst. vol. 68, 1968, 59481q.

*Primary Examiner*—Natalie Trousof
*Assistant Examiner*—Jane T. Fan
*Attorney, Agent, or Firm*—Cushman, Darby & Cushman

[57] ABSTRACT

A process for manufacture of 1-aryl-3-carboxypyrazolid-5-one compounds of the formula:

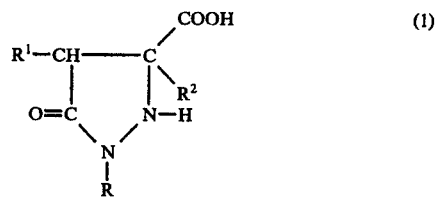

wherein $R^1$ and $R^2$ may be the same or different and each represents H or an alkyl, cycloalkyl, aralkyl or monocyclic aryl group or $R^1$ and $R^2$ together form a tetramethylene group; and R represents an aryl group which may be substituted which comprises reacting a hydrazine of the formula $R.NH.NH_2$ with an ester of the formula:

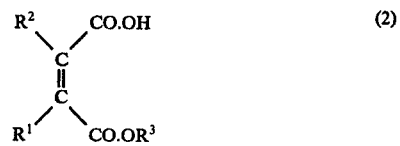

wherein $R^3$ is an alkyl, cycloalkyl, aralkyl or aryl group, which may be substituted.

The novel process provides better yields and simpler operating conditions than other processes described in the literature for manufacture of these pyrazolidones.

6 Claims, No Drawings

PROCESS FOR THE MANUFACTURE OF 1-ARYL-3-CARBOXYPYRAZOLID-5-ONES

This invention relates to a new process for the manufacture of heterocyclic compounds, more particularly heterocyclic compounds of the 1-aryl-3-carboxypyrazolid-5-one series.

According to the invention, there is provided a process for manufacture of 1-aryl-3-carboxypyrazolid-5-one compounds of the formula:

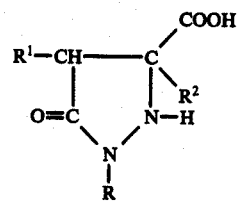  (1)

wherein $R^1$ and $R^2$ may be the same or different and each represents H or an alkyl, cycloalkyl, aralkyl or monocyclic aryl group or $R^1$ and $R^2$ together form a tetramethylene group, and R represents an aryl group which may be substituted which comprises reacting a hydrazine of the formula $R.NH.NH_2$ with an ester of the formula:

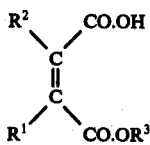  (2)

wherein $R^3$ is an alkyl, cycloalkyl, aralkyl or aryl group, which may be substituted.

As examples of alkyl groups represented by $R^1$, $R^2$ and $R^3$, there may be mentioned more especially alkyl groups of 1 to 4 carbon atoms, e.g. butyl, propyl, ethyl or methyl but also higher alkyl groups, e.g. hexyl, decyl, and octodecyl.

As examples of monocyclic aryl groups represented by $R^1$ and $R^2$ there may be mentioned phenyl and substituted phenyl e.g. tolyl, xylyl, chlorophenyl, nitrophenyl, carboxyphenyl and sulphophenyl.

As examples of aryl and substituted aryl groups represented by R or $R^3$ there may be mentioned those described for $R^1$ and $R^2$ in the preceding paragraph, also dicyclic aryl groups e.g. naphthyl, mono-,di- and tri-sulphonaphthyl, nitro-disulphostilbenyl, also diphenyl, diphenylamine, diphenyloxide, diphenyl sulphide, diphenylethane and their mono- or di-sulphonated derivatives. R is preferably phenyl or sulphophenyl.

As examples of cycloalkyl and aralkyl groups represented by $R^1$, $R^2$ or $R^3$ there may be mentioned cyclohexyl, benzyl and phenylethyl.

Thus, as examples of hydrazines of formula $R.NH.NH_2$, there may be mentioned:

Phenylhydrazine,
o-, m- and p-phenylhydrazine sulphonic acids,
2,4-, 2,5- and 3,5-disulphophenylhydrazines,
o-, m- and p-methylphenylhydrazines,
2-methyl-4- and 5-sulphophenylhydrazines,
4-methyl-2- and 3-sulphophenylhydrazines,
4-methyl-2,6-disulphophenylhydrazine,
4-methyl-5nitro-2-sulphophenylhydrazine,
o-, m- and p-nitrophenylhydrazines,
3-nitro-5-sulphophenylhydrazine,
2- and 3-nitro-4-sulphophenylhydrazines,
4-nitro-3-sulphophenylhydrazine,
o-, m- and p-methoxyphenylhydrazines
2-methoxy-4- and 5-sulphophenylhydrazines,
4-methoxy-2- and 3sulphophenylhydrazines,
4-methoxy-5-nitro-2sulphophenylhydrazine,
o-, m- and p-chlorophenylhydrazines,
2-chloro-4- and 5-sulphophenylhydrazines,
4-chloro-2- and 3-sulphophenylhydrazines,
o-, m- and p-carboxyphenylhydrazines,
2-carboxy-4- and 5-sulphophenylhydrazines,
1- and 2-naphthylhydrazines,
1-hydrazino-2-, 4- and 5-sulphonaphthalenes,
2-hydrazino-1-, 4-, 5- and 8-sulphonaphthalenes,
1-hydrazino-3,8- and 4,8-disulphonaphthalenes,
2hydrazino-1,5-, 4,8-, 5,7- and 6,8-disulphonaphthalenes,
1-hydrazino-3,6,8- and 4,6,8-trisulphonaphthalenes,
2hydrazino-1,5,7-, 3,6,8 and 4,6,8-trisulphonaphthalenes,
2-nitro-4'-hydrazinostilbene,
4-nitro-4'-hydrazino-2,2'-disulphostilbene,
2-, and 4-hydrazinodiphenyls,
2-, 3- and 4-hydrazinodiphenylamines,
4-hydrazino-2-sulphodiphenylamine,
4-hydrazino-2,2'-, 2,3'- and 2,4'-disulphodiphenylamines,
4-hydrazino-2-sulpho-2'-, 3'- and 4'-methyldiphenylamines,
3- and 4-hydrazino-2'-carboxydiphenylamines,
4-hydrazino-2-carboxydiphenylamine,
2-hydrazino-4-carboxydiphenylamine,
2-, 3- and 4-hydrazinodiphenylmethane,
2- and 4-hydrazinodiphenylsulphide.

As examples of esters of formula (2) there may be mentioned the mono-esters of the following acids and hydroxyl compounds:

Acids maleic acid
citraconic acid
dimethylmaleic acid
ethylmaleic acid
diethylmaleic acid
1-methyl-2-ethylmaleic acid
propylmaleic acid
1-methyl-2-butylmaleic acid
isobutyl-maleic acid
1-methyl-2isopropylmaleic acid
phenylmaleic acid
diphenylmaleic acid
cyclohex-1-ene-1,2-dicarboxylic acid Hydroxyl Compounds methanol
ethanol
propanol
isopropanol
n-butanol
n-hexanol
benzyl alcohol
phenylethyl alcohol cyclohexanol
phenol
o-, m- or p-sulphophenol.

The new process can be carried out in general by heating a mixture of the reactants, preferably in a solvent, which in the case of water-soluble reactants is preferably water. Where only one reactant is water-soluble the solvent is preferably a mixture of water with a water-miscible organic liquid inert to hydrazines such as ethanol or dimethylformamide.

Although a substantial excess of either reactant may be used, it is preferred to use approximately equal proportions, e.g. from 0 to 10% molar excess. In most cases formation of the pyrazolidone is accompanied by development of acidity and this may conveniently be neutralised by addition of an acid-binding agent as the reaction proceeds.

As a general rule it is preferred to use an ester of formula (2) in which $R^3$ represents an alkyl radical of 1 to 4 carbon atoms, above all a methyl radical, especially in the cases where $R^1$ and $R^2$ are both H since the monesters of maleic acid are readily obtainable by reaction of maleic anhydride with only a slight excess of the alcohol.

These compounds (i.e. in which $R^1$ and $R^2$ are both H but R has the meaning stated earlier) are useful intermediates in the dyestuffs industry since they can be converted by mild oxidation techniques to the corresponding 1-aryl-3-carboxypyrazol-5ones which are well known to be valuable as coupling components for the manufacture of a wide range of azo dyestuffs, e.g. of the acid, direct or reactive series. The new process provides better yields and simpler operating conditions than other processes described in the literature for manufacture of the pyrazolidones.

The invention may be illustrated by the following Examples in which parts are by weight:

EXAMPLE 1

110 parts of monomethyl maleate are added with stirring to 800 parts of water containing 152 parts of p-hydrazinobenzene sulphonate and 88 parts of sodium carbonate. The mixture is warmed until all reactants are in solution and the pH is adjusted by addition of sodium carbonate to 7.0. The resulting solution is heated at 100° C for 9 hours during which period the pH is adjusted to 7.0 after 6 hours. On completion of heating, the pH is adjusted to 3.8 by addition of hydrochloric acid and the 3-carboxy-1-(4'-sulphophenyl)-5-pyrazolidone thus formed is filtered off and dried between 50°–100° C. The actual weight yield is 266 parts of strength 77% (determined by N.M.R.) which represents a yield of 85% theory.

Two principal impurities have been detected namely
10% Fumaric Acid (determined by N.M.R. analysis) and
3.1% Unreacted p-hydrazinobenzene sulphonate determined by T.L.C. analysis in addition to an unquantified amount of sodium chloride generated in the reaction.

EXAMPLE 2

5 parts of monomethyl maleate are added with stirring to 25 parts of water containing 7 parts of p-hydrazinobenzene sulphonate and 4 parts of sodium carbonate and the mixture is heated at 100° C for 6 hours. The pH is then adjusted to 3.8 by addition of hydrochloric acid and the 3-carboxy-1-(4'-sulphophenyl)-5-pyrazolidone thus formed is filtered off and dried between 50°–100° C. The actual weight yield is 12 parts of strength 67% (determined by N.M.R.) which represents a yield of 73% theory.

EXAMPLE 3

2 parts of monoethyl maleate are added with stirring to 25 parts of water containing 2 parts of p-hydrazinobenzene sulphonate and 1 part of sodium carbonate. The mixture is heated at 100° C for 5 hours. The resulting solution is warmed with sodium carbonate and the pH finally adjusted to 3–4 with hydrochloric acid. The 3carboxy-1-(4'-sulphophenyl)-5-pyrazolidone thus formed is filtered off and dried between 50°–100° C. The actual weight yield is 4 parts of strength 74% (determined by N.M.R.) which represents a yield of 76%.

EXAMPLE 4

50 parts of monomethyl maleate are added with stirring to 400 parts of water containing 70 parts of p-hydrazinobenzene sulphonate and 39 parts of sodium carbonate. The mixture is warmed until all reactants are in solution and the pH is adjusted by sodium carbonate to 9.2. The resulting solution is heated at 100° C for 9 hours. On completion of heating, the pH is adjusted to 3.8 by addition of hydrochloric acid and the 3-carboxy-1-(4'-sulphophenyl)-5-pyrazolidone thus formed is recovered and dried between 50°–100° C. The actual weight yield is 140 parts of strength 70% (determined by N.M.R.) which represents a yield of 89% of the theory.

EXAMPLE 5

35 parts of mono n-propyl maleate are added with stirring to 200 parts of water containing 37.7 parts of p-hydrazinobenzene sulphonic acid and 21.2 parts of sodium carbonate. The mixture is then warmed until all reactants are in solution and the pH adjusted by sodium carbonate to 7.0.

The resulting solution is heated at reflux for 9 hours, during which period the pH is adjusted to 7.0 after 6 hours.

On completion of heating, the pH is adjusted to less than 3.0 with hydrochloric acid and the -carboxy-carboxy-1-(4'-sulphophenyl)-5-pyrazolidone thus precipitated is recovered and dried between 50°–100° C. The actual weight yield is 56.4 parts of strength 56.0% (determined by UV analysis) which represents a yield of 53.0% of theory.

EXAMPLE 6

35parts of mono n-Amyl maleate are added with stirring to 200 parts of water containing 32.1 parts of p-hydrazinobenzene sulphonic acid and 18 parts of sodium carbonate. The mixture is then warmed until all reactants are in solution and the pH adjusted to 7.0 with sodium carbonate.

The resulting solution is heated at reflux for 9 hours, during which period the pH is adjusted to 7.0 after 6 hours.

On completion of heating, the pH is adjusted to less than 3.0 with hydrochloric acid and the 3-carboxy-1-(4'-sulphophenyl)-5-pyrazolidone thus precipitated is recovered and dried between 50°–100° C. The actual weight yield is 33 parts of strength 61.5% (determined by UV analysis) which represents a yield of 40.2% of theory.

EXAMPLE 7

35 parts of mono benzyl maleate are added with stirring to 200 parts of water containing 30.4 parts of p-hydrazinobenzene sulphonic acid and 17.2 parts of sodium carbonate. The mixture is then warmed until all reactants are in solution and the pH is adjusted to 7.0 with sodium carbonate.

The resulting solution is heated at reflux for 9 hours during which period the pH is adjusted to 7.0 after 6 hours.

On completion of heating the pH is adjusted to less than 3.0 with hydrochloric acid and the 3-carboxy-1-(4'-sulphophenyl)-5-pyrazolidone thus precipitated is recovered and dried between 50°–100° C. The actual weight yield is 26 parts of strength 73.2% (determined by UV analysis) which represents a yield of 39.2% of theory.

EXAMPLE 8

130 parts of monomethyl maleate are added with stirring to 250 parts of water containing 108 parts of phenylhydrazine and 53 parts of sodium carbonate. The mixture is heated under reflux for 9 hours.

On completion of heating, the pH is adjusted to 3.0 with hydrochloric acid and the 3-carboxy-1-phenyl-5-pyrazolidone which separates is recovered by filtration and crystallised by tituration with methanol at room temperature.

The actual weight is 120 parts of strength 87.2% (determined by NMR) which represents a yield of 50.8% of theory.

EXAMPLE 9

20.3 parts of sodium monomethyl maleate in 50 parts of water are added with stirring to 150 parts of water containing 25 parts of p-tolylhydrazine. The mixture is then warmed until all reactants are in solution and the pH is adjusted to 5.5.

The resulting solution is heated under reflux for 12 hours. On completion of heating, the pH is adjusted to 3.0 with hydrochloric acid and the 3-carboxy-1-(4'-methylphenyl)-5-pyrazolidone which precipitates is recovered by filtration and dried in a vacuum desiccator.

The actual weight yield is 24.7 parts of strength 87.2% (determined by NMR) which represents a yield of 63.3% of theory.

What we claim is:

1. A process for the manufacture of a 1-aryl-3-carboxypyrazolid-5-one compound of the formula: Ser. No. 653,832 - Fleming et al

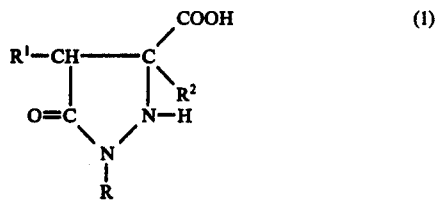

wherein $R^1$ and $R^2$ represent hydrogen and R represents phenyl; phenyl substituted with a member of the group consisting of methyl, chloro, nitro, carboxy and sulpho; naphthyl; sulphonaphthyl; nitro-disulphostilbenyl; diphenyl; diphenylamine; diphenyloxide; diphenyl sulphide; diphenylethane and their mono- or di-sulphonated derivatives which comprises heating, in an aqueous medium and in the presence of an acid-binding agent, a mixture of a hydrazine of the formula $R.NH.NH_2$ with an ester of the formula:

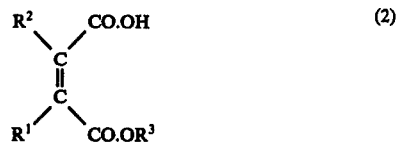

wherein $R_3$ is an alkyl, cycloalkyl, aralkyl or aryl group.

2. A process as claimed in claim 1 wherein $R^3$ is an alkyl radical of 1 to 4 carbon atoms.

3. A process as claimed in claim 2 wherein $R^3$ is methyl.

4. A process as claimed in claim 1 wherein R is phenyl.

5. A process as claimed in claim 4 wherein $R^3$ is methyl.

6. A process as claimed in claim 1 wherein R is sulphophenyl.

* * * * *